United States Patent
Bigalke et al.

(10) Patent No.: US 6,822,076 B2
(45) Date of Patent: Nov. 23, 2004

(54) HYBRID PROTEIN FOR INHIBITING THE DEGRANULATION OF MASTOCYTES AND THE USE THEREOF

(75) Inventors: Hans Bigalke, Hannover, DE (US); Jürgen Frevert, Berlin, DE (US)

(73) Assignee: BioteCon Therapeutics GmbH, Potsdam (DE)

( * ) Notice: Subject to any disclaimer, the term of this patent is extended or adjusted under 35 U.S.C. 154(b) by 37 days.

(21) Appl. No.: 10/064,903

(22) Filed: Aug. 27, 2002

(65) Prior Publication Data

US 2003/0059912 A1 Mar. 27, 2003

Related U.S. Application Data

(63) Continuation-in-part of application No. 09/700,540, filed as application No. PCT/EP99/03272 on May 12, 1999, now abandoned.

(30) Foreign Application Priority Data

May 13, 1998 (DE) .......................................... 198 21 285

(51) Int. Cl.[7] ................................................. C07K 1/00
(52) U.S. Cl. ....................... 530/350; 530/350; 530/300; 435/7.1; 424/192.1; 514/2; 514/12; 514/21
(58) Field of Search ................................. 530/350, 300; 435/7.1; 424/192.1; 514/2, 12, 21

(56) References Cited

U.S. PATENT DOCUMENTS 6,429,189 B1 * 8/2002 Borodic .......................... 514/2

OTHER PUBLICATIONS

Slater et al., The Journal of Immunology, vol. 140, pp. 807–811, 1988.*

* cited by examiner

*Primary Examiner*—Karen Cochrane Carlson
*Assistant Examiner*—Hope A. Robinson
(74) *Attorney, Agent, or Firm*—Gudrun E. Huckett

(57) ABSTRACT

A hybrid protein contains a protein that binds to a receptor of mastocytes and basophils and is endocyted by them. The protein can be IgE; IgE fragment; IgE Fc fragment; antibody against IgE receptor of mastocytes and basophils; fragment of the antibody against the IgE receptor of mastocytes and basophils; antibody against mastocyte specific potassium channel; and mast cell degranulating peptide. The hybrid protein also contains a protease cleaving proteins of the secretion process of the mastocytes and basophils so as to inhibit the secretion process without killing the mastocytes and basophils. The protease can be light chain *Clostridium botulinum* toxin; proteolytically active fragment of the light chain of a *Clostridium botulinum* toxin containing an amino acid sequence His-Xaa-Xaa-Xaa-His-Xaa-Xaa-His wherein Xaa is an amino acid; light chain of the tetanus toxin; proteolytically active fragment of the light chain of the tetanus toxin containing His-Asp-Leu-Ile-His-Val-Leu-His; IgA protease of *Neisseria gonorrhoeae*; and proteolytic domain of the IgA protease of *Neisseria gonorrhoeae*.

11 Claims, No Drawings

HYBRID PROTEIN FOR INHIBITING THE DEGRANULATION OF MASTOCYTES AND THE USE THEREOF

CROSS REFERENCE TO RELATED APPLICATIONS

This application is a continuation-in-part of U.S. patent application Ser. No. 09/700,540 filed Jan. 19, 2001 now abandoned (35 USC 102(e) date), which is the national stage of PCT/EP99/03272 having an international filing date of May 12, 1999.

BACKGROUND OF INVENTION

Allergic reactions of the immediate type are characterized in that the patients concerned have formed antibodies of the IgE type against allergens (for example, pollen, house dust, mites, animal hair). These antibodies circulate not only in the blood but also bind to cells present in the tissue exhibiting in the plasma membrane a specific receptor for a portion of the IgE molecule, the Fc fragment (Fishman & Lorberboum-Galski 1997; Hamawy 1997). Cells with the IgE receptors are mastocytes and basophils exclusively. These cells are the cells effecting the allergic reaction of the immediate type. The stored vesicles containing vasoactive amines and prostaglandins, leukotrienes (derivatives of the arachidonic acid), and other effector molecules such as chymase (=effector molecules of the allergic reaction). The secretion process causing the release of these substances and resulting in the degranulation of the mastocytes, occurs through a specific and an unspecific mechanism. Once cells are mechanically destroyed, e.g., by a scratch on the skin, histamine is unspecifically released. At the wound the skin turns red. Nettles (edemas) are formed and the skin itches (triple response). Substances releasing specifically histamine are effective in relatively low concentrations and trigger the following cascade of responses (signal cascade): activation of phospholipase C—formation of the second messengers "diacylglycerol" and "IP3"—mobilization of calcium from cellular depots—fusion of the granules (vesicles) with the cell membrane—exocytosis of the granules without cytolysis—exchange of sodium against the positively charged histamine of the complex with heparin and a basic protein—release of the histamine from the granule matrix.

Provided there is contact between the mastocytes of an allergic person and an allergen, the IgE molecules on the cell surface bind this allergen. Once allergen molecules are bound in sufficient amounts, aggregation of the receptors in the plasma membrane occurs. The aggregation is the specific stimulus for the induction of the above described signal cascade in the interior of the cell. The substances released induce the allergic symptoms (conjunctivitis, rhinitis, asthma, laryngeal edema, urticaria, blood pressure drop up to a pronounced anaphylactic shock). Peptides contained in the toxin of the bee such as the mast cell degranulating peptide (MCD) also effect a degranulation of the mastocytes. Additionally, some pharmaceuticals cause a specific release of histamine as an undesired effect. The release of histamine in humans is described for muscle relaxing agents, dextrans, acetylsalicylic acid (aspirin), morphine, antibiotics, contrast media in radiography, foreign sera etc.

If in the secretion process the fusion of the vesicles with the plasma membrane is successfully inhibited, then there is no release of the amines and arachidonic acid derivatives. Consequently, no allergic reactions are induced. Several proteins (fusion proteins) are involved in the secretion process and the release, respectively, which proteins may be bound to membranes of secretory vesicles and/or to the plasma membrane. Likewise, they may appear in the cytosol. Representatives of these proteins are SNAP 25, synaptobrevin (V AMP), syntaxins and its isoforms, respectively. These proteins form a complex (fusion complex) fixating the secretory vesicles to the inner side of the plasma membrane. The fixation precedes the fusion of the vesicles with the plasma membrane and subsequent release of histamine and other effector molecules. By inactivation of one of these proteins, for example, by proteolytic cleavage, the formation of the complex is inhibited and the secretion process interrupted. As a consequence, the mast cells cannot release anymore the content of the vesicles (amines, arachidonic acid, arachidonic acid derivatives, etc.).

From nerve cells it is known that the fusion proteins (SNAP 25, synaptobrevin and syntaxin) mentioned are the target molecules (substrates) of the light chains of the neurotoxins produced by the bacterium *Clostridium botulinum* in the nerve cells (Ahnert& Bigalke, 1995; Bigalke 2000). At present, seven different types of *botulinum* toxins are known (A, B, C1, D, E, F, and G). The synaptobrevin mentioned additionally is a target molecule for TeNT (Link et al., 1993) produced by *Clostridium tetani*, and also for a protease from *Neisseria gonorrhoeae* (Binscheck et al., 1995). The toxins, apart from the latter, consist of at least two functional domains. The C terminal portion of the protein (heavy chain) is responsible for its binding to the nerve cell whilst the N terminus (light chain) is characterized by the above described highly specific proteolytic activity. The toxins bind to nerve cells via their heavy chain and reach the cytosol via a receptor mediated endocytosis and subsequent translocation, where they cleave one or more of the fusion proteins (SNAP 25, synaptobrevin or syntaxin) which, in turn, are constitutive for the fusion complex. After the cleavage of the respective protein, the secretion of acetylcholine and other transmitters, respectively, from the nerve cells is inhibited (Binscheck and Wellh ö ner, 1997).

The inhibition of the release of transmitters has been therapeutically used in the past for the treatment of dystonic motor disturbances and for the suppression of excessive parasympathic activities (Benecke and Kessler, 1995). For the *clostridial* neurotoxins biological substrates other than the fusion proteins are not known. The heavy chains have a high affinity for peripheral nerve cells such that the light chains connected to them reach only these cells and become effective only in these cells although other cell types, such as mastocytes and basophils, in which the above described secretion processes occur, possess the above mentioned substrates of these proteases (light chains of the neurotoxins); however, they do not possess a mechanism for the uptake of the protease (Marxen et al., 1989).

To act on the secretory process in mast cells and basophils, it is therefore necessary to substitute a protein, which provides a specific binding to mast cells and basophils, for the heavy chain of the neurotoxin(s).

SUMMARY OF INVENTION

One embodiment of the present invention relates to a hybrid protein, comprising or consisting of
  (i) a protein known in the art, said protein binding to mastocytes and/or basophils and/or being taken up (endocyted) by these cells as is known in the art,
  (ii) a protease known in the art, said protease cleaving one or several proteins of the secretion process of the mastocytes and/or basophils.

A further embodiment of the present invention relates to a hybrid protein comprising or consisting of
(i) a protein binding to mastocytes and/or basophils and/or being taken up (endocyted) by these cells, wherein the protein (i) is selected from the group consisting of: IgE;
IgE fragment, in particular, IgE Fc fragment;
antibody against IgE receptor of mastocytes and/or basophils; fragment of the antibody against IgE receptor of mastocytes and/or basophils, in particular Fab fragment; antibody against mastocyte specific potassium channel; and
inactive but binding MCD peptide; and
(ii) a protease, in particular a protease known in the art, cleaving one or several proteins of the secretion process of the mastocytes and/or basophils.

Yet another embodiment of the present invention relates to a hybrid protein comprising or consisting of
(i) a protein, in particular a protein known in the art, said protein binding to mastocytes and/or basophils and/or being taken up (endocyted) by these cells, in particular in a manner known in the art; and
(ii) a protease, said protease cleaving one or several proteins of the secretion process of the mastocytes and/or basophils, wherein the protease (ii) is selected from the group consisting of:
light chain of a *Clostridium botulinum* toxin, in particular, the toxins of type A, B, C1, D, E, F, and G;
proteolytically active fragment of the light chain of a *Clostridium botulinum* toxin, in particular a toxin of the type A, B, C1, D, E, F, end G, characterized by containing the sequence SEQ ID NO:1 His-Xaa-Xaa-His-Xaa-Xaa-His, where Xaa can be any amino acid (for example, Xaa can be Leu, Ile, Val, Arg, Met);
light chain of the tetanus toxin (TeNT);
proteolytically active fragment of the light chain of the tetanus toxin, characterized by containing the sequence SEQ ID NO:2 His-Asp-Leu-Ile-His-Val-Leu-His;
IgA protease of *Neisseria gonorrhoeae*.

The hybrid protein of the present invention is characterized in that the protein (i) and the protease (ii) are selected from the previous groups of proteins and proteases, respectively.

In the sequence of SEQ ID NO:1 His-Xaa--Xaa-Xaa-His-Xaa-Xaa-His of the proteolytically active fragment of the light chain of a *Clostridium botulinum* toxin, the first Xaa is preferably Asp or Ala; the second Xaa is preferably Leu or Ile; the third Xaa is preferably Ile, Asn or Tyr and the fourth and fifth Xaa are preferably an amino acid with a non-polar functional group, i.e., amino acids such as Val, Leu, Ile, or Ala, respectively.

The hybrid protein of the present invention is additionally characterized in that the N-terminal portion of the heavy chain of the respective toxin ($H_N$ fragment) or a fragment thereof is part of the hybrid protein, in addition to the light chain of a *Clostridium botulinum* toxin or of the tetanus toxin.

Finally, one embodiment of the present invention relates to the use of the present hybrid protein to inhibit the degranulation of mastocytes.

If mastocytes were killed, there would exist the danger that an allergic shock would be induced once the dying mastocytes release the stored endogenous amines. Additionally, the drop of the number of mastocytes would stimulate the de novo synthesis of these cells which, in turn, would be available again for allergic reactions. The hybrid protein of the present invention is thus fundamentally different from the IgE pseudomonas exotoxin conjugate inhibiting protein synthesis by its ADP ribosylation activity and thus effecting cell death (Fishman & Lorberboum 1997). Quite conversely, the hybrid protein of the present invention does not serve to kill mastocytes. Rather, the cells remain vital after having been subjected to the hybrid protein of the present invention and have lost no more than their capacity to release vasoconstrictive amines.

A stimulation of the de novo synthesis does not occur. When therapeutically used, conceivable toxic side effects to be expected with a conjugate based on the complete cytotoxic pseudomonas toxin or a comparable cytotoxin are avoided.

Subject matter of the invention is thus a conjugate (hybrid protein) consisting of (i) a protein or peptide (transport protein/peptide) exhibiting a high affinity to mastocytes/basophils and (ii) a specific protease, which conjugate blocks the degranulation and the secretory mechanism, respectively, of the cells. The conjugate is useful for the therapy/prophylaxis of allergic reactions of the immediate type.

(i) Preferred high-affinity mastocyte binding components of the conjugates are immunoglobulins of type E (IgE) and its fragments (e.g., the Fc fragment) respectively. Additionally, antibodies against specific surface molecules of mastocytes/basophils are used, which antibodies selectively bind to the plasma membrane of these cells. Above all, antibodies against the IgE receptor fulfill this purpose. Furthermore, inactive but binding mutants of the mast cell degranulating peptide are to be used as transport peptides/proteins in the hybrid protein. These transport peptides/proteins are useful to channel a protease into the cells. This protease cleaves proteins in the fusion complex of mastocytes in a highly specific manner, which proteins initiate the degranulation mechanism of the cells.

(ii) Useful as a highly specific protease is a metalloprotease, e.g., the light chain of *botulinum* toxin of type A, B, C1, D, E, F, or G (BoNT/X) and of the tetanus toxin (TeNT) or the IgA protease of *Neisseria gonorrhoeae*. These proteases cleave the synaptosomal associated protein ($M_R$ 25,000) (SNAP 25), synaptobrevin or syntaxin. If only one of these proteins/peptides is cleaved, the degranulation of the mastocytes is inhibited. As a result, no secretion of histamine, prostaglandins, and leukotrienes will occur, and allergic symptoms cannot occur anymore.

In the present invention the nontoxic light chains of the toxins can be attached to transport proteins exclusively binding to mastocytes and basophils, respectively, and thus, can be taken up only by these cells, wherein the light chains, as if carried along as a passenger, reach the cells. They cannot invade nerve cells and cells of other type of the organism such that the effect is limited to mastocytes and basophils. If one of the substrates is proteolytically destroyed, no allergic symptoms occur subsequent to the contact of these IgE loaded cells with an allergen or with one of the above mentioned pharmaceuticals.

Useful as proteins specifically binding to mastocytes are
1) immunoglobulins of type E and their fragments of the type Fc;
2) antibodies against the IgE receptor;
3) the mast cell degranulating peptide; and
4) an antibody against the mastocyte specific potassium channel.

In regard to the protein listed, reference is made to the following publications:

IgE: Helman (1995)

IgE fragment: Helman (1995)

Antibody against IgE receptor of mastocytes/basophils, antibodies against mastocyte specific potassium channel, Fab fragment of the antibody: these are standard procedures described in: Liddel & Weeks (1995)

MCD peptides: Gmachel & Krell (1995)

Inactive but binding mutant: The mutated peptide is prepared according to standard procedures: Nichol D. S. T. (1995)

Light chains of the various *botulinum* toxins of type A–G: Binz et al. (1990)

Light chain of tetanus toxin: Eisel et al. (1989)

IgA protease: Bruscheck et al. (1995)

The connection of both components (transport protein and protease) occurs via different routes: First, the light chain of the toxin is chromatographically purified. The light chain is entirely nontoxic because, after its separation from the heavy chain, the neurotropic transport protein, it cannot reach the nerve cells and an extracellular substrate does not exist. The light chain is then chemically bound to one of the four mastocyte binding proteins to form a conjugate which, in turn, is taken up (endocyted) in the cytosol of mastocytes. The light chain cleaves its substrate there, which cleavage inhibits the secretion of histamine and other substances. A second way to prepare the conjugate is to fuse the gene for the light chain and the gene for one of the four mastocyte binding proteins such that a hybrid protein is expressed in suitable host cells. This biotechnologically produced hybrid protein should block the secretory process from mastocytes in analogy to the conjugate prepared from two protein components.

The preparation of hybrid proteins is a procedure known in the art, in particular in the field of tumor therapy (Vogel, 1987; Magerstadt, 1991). In this therapeutic concept an antibody against surface proteins of the tumor cells are attached to a cytotoxic protein, e.g., ricin, diphtheria toxin, to kill cancer cells. The novel aspect in the method of the present invention is the use of specific proteases and proteolytic domains, respectively, in hybrid proteins for the inhibition of the degranulation of mastocytes and, thus, for an anti allergen therapy. These hybrid proteins were not only useful to avoid heavily impairing allergic symptoms (hay fever, asthma, and neurodermitis). They could be administered also prophylactically to avoid allergic reactions during therapies with life saving pharmaceuticals. Moreover, they could avoid allergic symptoms occurring in the course of desensitization.

DETAILED DESCRIPTION

The invention will now be described in detail with the aid of specific non-limiting examples.

EXAMPLE 1

Synthesis of a Hybrid Protein from IgE and the Light Chain of BoNT/A

The purified *botulinum* toxin (5.0 mg) of type A was applied, after equilibration in 15 mM sodium tetraborate and 30 mM phosphate pH 8.4, to a QAE Sephadex column (1.0×3.0 cm), equilibrated with the same buffer. The column was subsequently washed with 10 ml 120 mM dithioerythrol, 2 M urea and 1 mM EDTA and incubated over night. Thereafter, the light chain was eluted from the column by means of 10 mM borate buffer and dialyzed against 20 mM phosphate pH 7.0.

Immunoglobulin E (rat) was purchased. 10 mg of the immunoglobulin were cleaved with 50 µg papain in 1 ml phosphate buffer (4 degrees C. over night). The Fc fragment was purified over a gel filtration column (Sephacryl S200). 3.0 mg of the purified Fc fragment were incubated with 3.0 mg of a purified light chain of *botulinum* toxin with 10 mM dithio bis succinimidyl propionate (bifunctional agent) in 2 ml Na phosphate, pH 7.0, over a period of 16 hours. The hybrid protein thus synthesized was purified via gel filtration (Sephacryl S200) and analyzed for its purity via SDS gel electrophoresis.

The inhibition of the degranulation of the mastocytes is examined in two experimental approaches. In the first approach isolated mastocytes of the rat are incubated with the hybrid molecule. Thereafter the release of histamine is stimulated. The stimulation occurs with specific histamine liberators such as the MCD peptide and concanavalin A (the latter being an experimentally utilized substance) and by a direct increase of the intracellular calcium concentration, respectively. The latter is achieved by an injection of calcium into distinct mastocytes. Thus, one shortcircuits the above described signal cascade as the increase of the calcium concentration is the step during the secretion process which is followed by the fusion of the vesicles. The degranulation of the mastocyte reflecting the release of histamine is followed in the phasecontrast microscope. Subsequently, it is possible to quantify released histamine by means of a measurement of the fluorescence. Finally, the enlargement of the mastocyte caused by the incorporation of vesicle membranes into the plasma membrane during degranulation can be determined electrophysiologically. In the cells treated with hybrid protein there will, in contrast to control cells, occur (1) no morphological change, (2) no enhancement of the fluorescence in the supernatant of the cell, and (3) no enlargement of the cell. Thereby it is possible to prove that the release of histamine is blocked by the hybrid protein.

In the second experimental approach the hybrid protein is injected into living rats. The rats are killed after several days and their mastocytes conventionally isolated. The degranulation and release of histamine, respectively, is determined as described above. In this approach it is examined whether the conjugate is able to reach the compartment also in the living animal, in which compartment the mastocytes are located in, and whether the conjugate inactivates the mastocyte in the living animal.

EXAMPLE 2

Production of a Recombinant Hybrid Protein by Operably Linking the Gene Encoding the Light Chain of *Clostridium botulinum* Type A to the Gene Encoding Immunoglobulin E and one of its Fragments (Fc fragment), Respectively The gene encoding the light chain of *botulinum* toxin type A is isolated by means of suitable primers via PCR (polymerase chain reaction). A culture of *Clostridium botulinum* type A is prepared from which the DNA is prepared. From the published sequence of the toxin gene (Binz et al., 1990) a pair of primers is derived and the gene for the light subunit amplified via PCR. Thereafter this gene is cloned into a commercial expression vector pQE according to the recipe of the producer.

The gene encoding the Fc fragment of the human immunoglobulin E (Helman, 1995 L.) was isolated via PCR from a commercial cDNA library and fused in the vector construct with the gene light chain of *botulinum* toxin type A.

With this construct competent M15 cells (*E. coli*) are transformed. As in this expression system the inserted genes are equipped with a "his tag". The recombinant protein is purified through affinity chromatography over a Ni NTA column (Quiagen). The process of highly purifying the protein is followed by a gel filtration through Sephacryl S300.

The measurement of the biological activity was performed again on isolated mastocytes in vitro.

EXAMPLE 3

Preparation of a Recombinant Hybrid Protein by Operably Linking the Gene Encoding the Light Subunit of the Tetanus Toxin with a Mutated Gene Encoding the Mast Cell Degranulating Peptide (MCD)

The "sequence for the mast cell degranulating peptide", a 22 mer, is known (Gmachl and Kreil, 1995). Based thereon a corresponding oligonucleotide is synthesized.

In order to isolate the sequence of the light subunit of the tetanus toxin a culture of *C. tetani* was prepared and DNA recovered therefrom. From the known nucleic acid sequence of the tetanus toxin a primer for PCR and hence the gene for the light subunit of the toxin was obtained.

As described in Example 1, both nucleic acid sequences were fused in an expression vector pQU and subsequently expressed in *E. coli*. The hybrid protein which, in turn, was equipped with a "his tag" was purified through affinity chromatography and subsequent gel filtration. The purified gene encoding the mast cell degranulating peptide is chemically synthesized including a point mutation in the active domain of the peptide. The gene is operably linked to the gene encoding the light chain of the tetanus toxin. The hybrid protein is expressed in *E. coli* and purified. The thus produced hybrid protein is tested in vitro in the mastocyte degranulation assay.

EXAMPLE 4

Preparation of a Recombinant Hybrid Protein by Linking the Gene Encoding the Fc Fragment of IgE to the Gene Encoding the IgA Protease The gene encoding the Fc fragment of IgE was isolated as described in Example 1.

The gene encoding the IgA protease from *N. gonorrhoeae* is known. Primers were derived therefrom, and the gene encoding the specific protease was recovered by means of PCR from a nucleic acid preparation obtained from *N. gonorrhoeae*.

Both nucleic acids were integrated into a commercial vector following the recipe giving by the producer and the hybrid protein purified by affinity chromatography (see Example 2).

The inhibitory activity is again proven in vitro on isolated mastocytes (see above).

EXAMPLE 5

Preparation of a Hybrid Protein Consisting of the Fab Fragment of an Antibody Against the IgE Receptor and the Light Chain of Botulinum Toxin Type B A monoclonal antibody against the IgE receptor on mastocytes was purchased and chromatographically repurified. 0.5 mg of the antibody were conjugated to 0.4 g of the purified light chain of *botulinum* toxin F. The light subunit was isolated by cleavage of the neurotoxin and subsequent purification through ion exchange chromatography, once the preparation of the neurotoxin had been performed according to the procedure in Example 1.

Both proteins (light subunit of toxin type F and monoclonal antibody) were linked to each other by using a bifunctional agent. The isolated proteins were incubated with 10 mM maleimido benzoyl N hydroxy succinimide ester for this purpose. The hybrid protein was subsequently purified from nonconjugated proteins by gel filtration over Sephacryl S300.

Again, isolated mastocytes were used to demonstrate that the hybrid protein synthesized inhibited the secretion of histamine.

Patent-related documents of interest in this connection are: U.S. Pat. No. 4,902,495 (IgE Fc directed delivery systems) and PCT application WO 94/21300 (Novel Agent Controlling Cell Activity)

References:

1) Ahnert G., Bigalke H. (1995); Molecular aspects of tetanus and *botulinum* neurotoxin poisoning. Progress in Neurobiology 46: 83ff 2) Benecke R., Kessler K. R. (1995); Botulinum toxin A; Akt. Neurol 22: 209ff 3) Bigalke, H. & Shoer, L. F. (2000); Clostridial Toxins, Handbook of Experimental Pharmacology and Toxicology; Ed. Just & Aktories, Springer Verlag, pp. 407-443

4) Binscheck T., Bartels F., Bergel H., Bigalke H., Yamasaki S., Hayashi T., Niemann H., Pohlner J. (1995); IgA protease from *Neisseria gonorrhoeae* inhibits exocytosis in bovine chromaffin cells like tetanus toxin; J. Biol. Chem. 270: 1770ff 5) Binscheck T., Wellh ö ner H. H. (1997); Tetanus and *botulinum* toxins zinc proteases synaptotagmin exocytosis. In: Toxins and signal transduction; (Eds.: Gutman Y., Lazarovici P.) 1: 457ff 6) Binz, T., Kurazono, H., M., Frevert, J., Wernars K. & Niemann, H. (1990); The complete sequence of *botulinum* toxin A and comparison with other *clostridial* neurotoxins; J. Biol. Chem. 265: 9153ff 7) Cardoso, F. & Jancovic, J. (1995); Clinical use of *botulinum* neurotoxins; Current Topics Microbiol. Immunol. 195: 123ff 8) Fishman, A., Lorberboum-Galski H. (1997); Targeted elimination of cells expressing the high affinity receptor for IgE (Fc epsilon RI) by a Pseudomonas exotoxin based chimeric protein; Eur. J. Immunol., 27: 486ff 9) Gmachl, M. & Kreil, G. (1995); The precursors of the bee venom constituents apamin and MCE peptide are encoded by two genes in tandem which share the same 3' exon; J. Biol. Chem 270 (21): 12704ff 10) Helman, L. (1995); Characterization of four novel epsilon chain mRNA and a comparative analysis of genes for immunoglobulin E in rodents and man; Eur. J. Immunol. 23 (1): 159ff 11) Liddel & Weeks (1995); Antik ö rper Techniken; Spektrum Akademischer Verlag Heidelberg 12) Link E., Edelmann L., Chou J., Binz T., Yamasaki S., Eisel U., Baumert M., S ü dhof T. C., Niemann H. & Jahn R. (1992); Tetanus toxin action: Inhibition of neurotransmitter release linked to synaptobrevin proteolysis; Biochem. Biophys. Res. Comm. 189: 18423ff 13) Magerstadt, M. (1991); Antibody conjugates and malignant diseases; CRC Press 14) Hamawy M. M. (Ed.) (1997); IgE Receptor (FceRI) Function In: Mast Cells and Basophils; Springer Verlag 15) Marxen P., Fuhrmann U., Bigalke H. (1989); Gangliosides mediate inhibitory effects of tetanus and *botulinum* A neurotoxins on exocytosis in chromaffin cells; Toxicon 27: 849

16) Nichols D. S. T. (1995); Gentechnische Methoden; Spektrum Akademischer Verlag 17) Vogel, C.(Ed.) (1987); Immunoconjugates: Antibody conjugates in radioimaging and therapy of cancer; Oxford UP Inc.

What is claimed is:

1. A hybrid protein comprising:

(i) protein capable of binding to a receptor at least one cell type selected from the group consisting of mastocytes and basophils and of being endocyted by the at least one cell type selected from the group consisting of the *mastocytes* and *basophils:*

(ii) a protease capable of cleaning one or more secreted proteins of the at least one cell type selected from the group consisting of the *mastocytes* and *basophils* so as to inhibit the secretion process without killing the at least one cell type selected from the group consisting of the *mastocytes* and *basophils*, wherein the protease (ii) is selected from the group consisting of:

light chain of a *Clostridium botulinum* neurotoxin;

proteolytically active fragment of the light chain of a *Clostridium botulinum* neurotoxin containing an amino acid sequence of SEQ ID NO:1 His-Xaa-Xaa-Xaa-His-Xaa-Xaa-His, wherein Xaa is any amino acid.

light chain of the tetanus toxin (TeNT);

proteolytically active fragment of the light chain of the tetanus toxin containing an amino acid sequence of SEQ ID NO:2 His-Asp-Leu-lIe-His-Val-Leu-His;

IgA protease of *Neisseria gonorrhoeae*; and proteolytic domain of the IgA protease of *Neisseria gonorrhoeae*.

2. The hybrid protein according to claim 1, wherein the *Clostridium botulinum* neurotoxin is of type A, B, C1, D, E, F, or G.

3. The hybrid protein according to claim 1, wherein the protein (i) is selected from the group consisting of:

IgE;

IgE fragment;

IgE Fc fragment;

antibody against IgE receptor of the at least one of the mastocytes and basophils; fragment of the antibody against the IgE receptor of the at least one of the *mastocytes* and *basophils*; antibody against mastocyte-specific potassium channel; and MCD (mast cell degranulating) peptide.

4. The hybrid protein according to claim 3, wherein the fragment of the antibody against the IgE receptor of the at least one of the *mastocytes* and *basophils* is a Fab fragment.

5. The hybrid protein according to claim 3, further comprising the N-terminal portion of a heavy chain of a neurotoxin ($H_N$ fragment) or a fragment thereof in addition to the light chain of a *Clostridium botulinum* neurotoxin or of the tetanus toxin.

6. A hybrid protein comprising:

(i) a protein capable of binding to a receptor of at least one cell type selected from the group consisting of mastocytes and basophils and of being endocyted by the at least one cell type selected from the group consisting of the mastocytes and basophils, wherein the protein is selected from the group consisting of:

IgE;

IgE fragment:

IgE Fc fragment;

antibody against IgE receptor of the at least one cell type selected from the group consisting of the *mastocytes* and *basophils*; fragment of the antibody against the IgE receptor of the at least one cell type selected from the group consisting of the *mastocytes* and *basophils*; antibody against *mastocytel -specific potassium channel; and*

MCD (mast cell degranulating) peptide; and (ii) a protease capable of cleaving one or more secreted of the at least one cell type selected from the group consisting of the *mastocytes* and *basophils* so as to inhibit the secretion process without killing the at least one cell type selected from the group consisting of the *mastocytes* and *basophils*, wherein the protease is selected from the group consisting of:

light chain of a *Clostridium botulinum* toxin neurotoxin;

proteolytically active fragment of the light chain of a *Clostridium botulinum* neurotoxin containing an amino acid sequence of SEQ ID NO:1 His-Xaa-Xaa-Xaa-His-Xaa-Xaa-His wherein Xaa is any amino acid;

light chain of the tetanus toxin (TeNT);

proteolytically active fragment of the light chain of the tetanus toxin containing an amino acid sequence of SEQ ID NO :2 His-Asp-Leu-lIe-His-Val- Leu-His;

IgA protease of *Neisseria gonorrhoeae*; and proteolytic domain of the IgA protease of *Neisseria gonorrhoeae.*

7. The hybrid protein according to claim 6, wherein the fragment of the antibody against the IgE receptor of the at least one of the mastocytes and basophils is a Fab fragment.

8. The hybrid protein according to claim 6, wherein the *Clostridium botulinum* neurotoxin is of type A, B, C1, D, E, F, or G.

9. The hybrid protein according to claim 6, further comprising the N-terminal portion of a heavy chain of a *botulinum* neurotoxin or a tetanus toxin ($H_N$ fragment) or a fragment of the N-terminal portion of the heavy chain of the *botulinum* neurotoxin or the tetanus toxin in addition to the light chain of the *Clostridium botulinum* neurotoxin or of the tetanus toxin.

10. A method of inhibiting degranulation of mastocytes and basophils by administering an effective amount of a hybrid protein according to claim 1.

11. A method of inhibiting degranulation of mastocytes and basophils by administering an effective amount of a hybrid protein according to claim 6.

* * * * *